United States Patent [19]

Allen

[11] Patent Number: 4,991,091

[45] Date of Patent: Feb. 5, 1991

[54] SELF-CONTAINED EXAMINATION GUIDE AND INFORMATION STORAGE AND RETRIEVAL APPARATUS

[76] Inventor: Gregory Allen, 411 S. Woodward #526, Birmingham, Mich. 48011

[21] Appl. No.: 235,154

[22] Filed: Aug. 23, 1988

[51] Int. Cl.⁵ .................................................. G06F 15/42
[52] U.S. Cl. .................................. 364/413.02; 364/200
[58] Field of Search ...................... 364/413.02, 200, 900

[56] References Cited

U.S. PATENT DOCUMENTS

| | | |
|---|---|---|
| Re. 27,580 | 2/1973 | Rawson et al. |
| 3,566,370 | 2/1971 | Worthington, Jr. et al. |
| 3,829,844 | 8/1974 | Zonneveld et al. |
| 3,942,157 | 3/1976 | Azure ........................ 364/900 |
| 3,970,996 | 7/1976 | Yasaka et al. |
| 4,130,881 | 12/1978 | Haessler .................. 364/413.02 |
| 4,150,284 | 4/1979 | Trenkler et al. |
| 4,290,114 | 9/1981 | Sinay . |
| 4,428,382 | 1/1984 | Walsall et al. |
| 4,481,412 | 11/1984 | Fields ........................ 235/383 |
| 4,491,725 | 1/1985 | Pritchard ................. 364/406 |
| 4,611,298 | 9/1986 | Schuldt ..................... 364/900 |
| 4,667,292 | 5/1987 | Mohlenbrock ........ 364/200 |
| 4,731,725 | 3/1988 | Suto et al. |
| 4,733,354 | 5/1988 | Potter et al. ............. 304/413.02 |
| 4,839,822 | 6/1989 | Domond et al. |

OTHER PUBLICATIONS

"Computers in Critical Care", John E. Brimm, Brochure from Emtek Health Care Systems, Mar. 1987.
"Better Care, Shorter Stays, Thanks to Networding", Data Communications, Nov. 1986, Principi et al., Nov. 1986.

Primary Examiner—Michael R. Fleming
Assistant Examiner—Gail O. Hayes
Attorney, Agent, or Firm—Barnes, Kisselle, Raisch, Choate, Whittemore & Hulbert

[57] ABSTRACT

Self-contained examination guide and information storage apparatus comprising a flat rectangular enclosure having a front panel with first display arrays along side edges of the front panel associated with a plurality of general patient examinatin categories, and an LCD centrally positioned on the front panel and configured to comprise a plurality of individually controllable display segments. A microprocessor-based controller includes a light pen for reading bar codes on the enclosure front panel and thereby selecting among the general examination categories. A microcontroller memory has prestored sets of specific examination indicia associated with each of the general examination categories, and is responsive to the category-selection process for retrieving from memory a specific set of examination indicia associated with selected general examination category. The light pen is then employed to scan bar code arrays adjacent to the specific examination indicia at each LCD segment for identifying specific indicia of interest and loading corresponding indicia information into microcontroller memory. Information so stored may be selectively downloaded to a central computer for processing and generation of records for the patient files.

37 Claims, 3 Drawing Sheets

FIG. 4

SELF-CONTAINED EXAMINATION GUIDE AND INFORMATION STORAGE AND RETRIEVAL APPARATUS

The present invention is directed to apparatus assisting or guiding examination or inspection in accordance with predetermined examination categories, and more particularly to self-contained apparatus for guiding a physician during patient examination and recording information as observed and entered ,by the physician.

BACKGROUND AND OBJECTS OF THE INVENTION

It is a general object of the present invention to provide self-contained apparatus for guiding examination in accordance with predetermined examination categories which is battery-operated for enhanced mobility, which is easy to use, which may be readily reprogrammed to alter or modify examination information, and/or which produces a permanent record of examination results.

Another and more specific object of the invention is to provide apparatus of the described character which is particularly adapted to assist a physician in conducting a patient examination, which enhances efficiency and economy of the examination process, and which produces a clear and legible permanent record for the patient file.

A further object of the invention is to provide apparatus of the described character which may be employed in a centralized information storage and retrieval system to download examination information from one or more remote stations distributed around a medical office or hospital complex.

BRIEF DESCRIPTION OF THE DRAWINGS

The invention, together with additional objects, features and advantages thereof, will be best understood from the following description, the appended claims and the accompanying drawings in which:

FIG. 4 is an elevational view of the operator panel in apparatus in accordance with the present invention illustrating an exemplary examination screen.

DETAILED DESCRIPTION OF PREFERRED EMBODIMENTS

Figure 1:
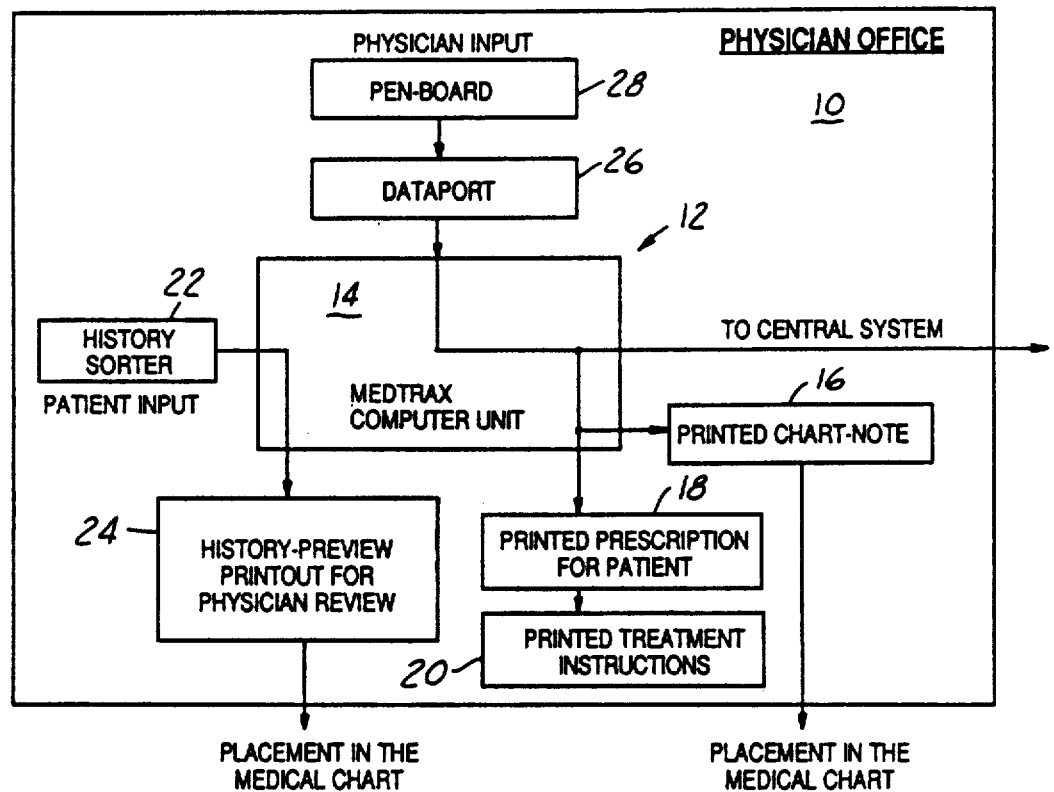
FIG. 1 is a functional block diagram of a physician office complex in which a centralized patient information storage and retrieval system is implemented in accordance with the principles of the present invention.

FIG. 1 is a functional block diagram of a physician's office complex 10 embodying a centralized patient information storage and retrieval system 12 in accordance with a presently preferred embodiment of the invention. System 12 includes a central computer 14 having internal memory and suitable control programming for driving a printer to generate a chart note 16 for placement in the patient file, for printing patient prescriptions 18 and corresponding treatment instructions 20, and for receiving patient history input 22 from a patient or medical technician and generating a corresponding history hardcopy 24 for placement in the patient file. In accordance with a principal feature of the present invention, central computer 14 also receives input from one or more dataports 26, which in turn are electronically coupled to corresponding penboards 28.

Figure 2:
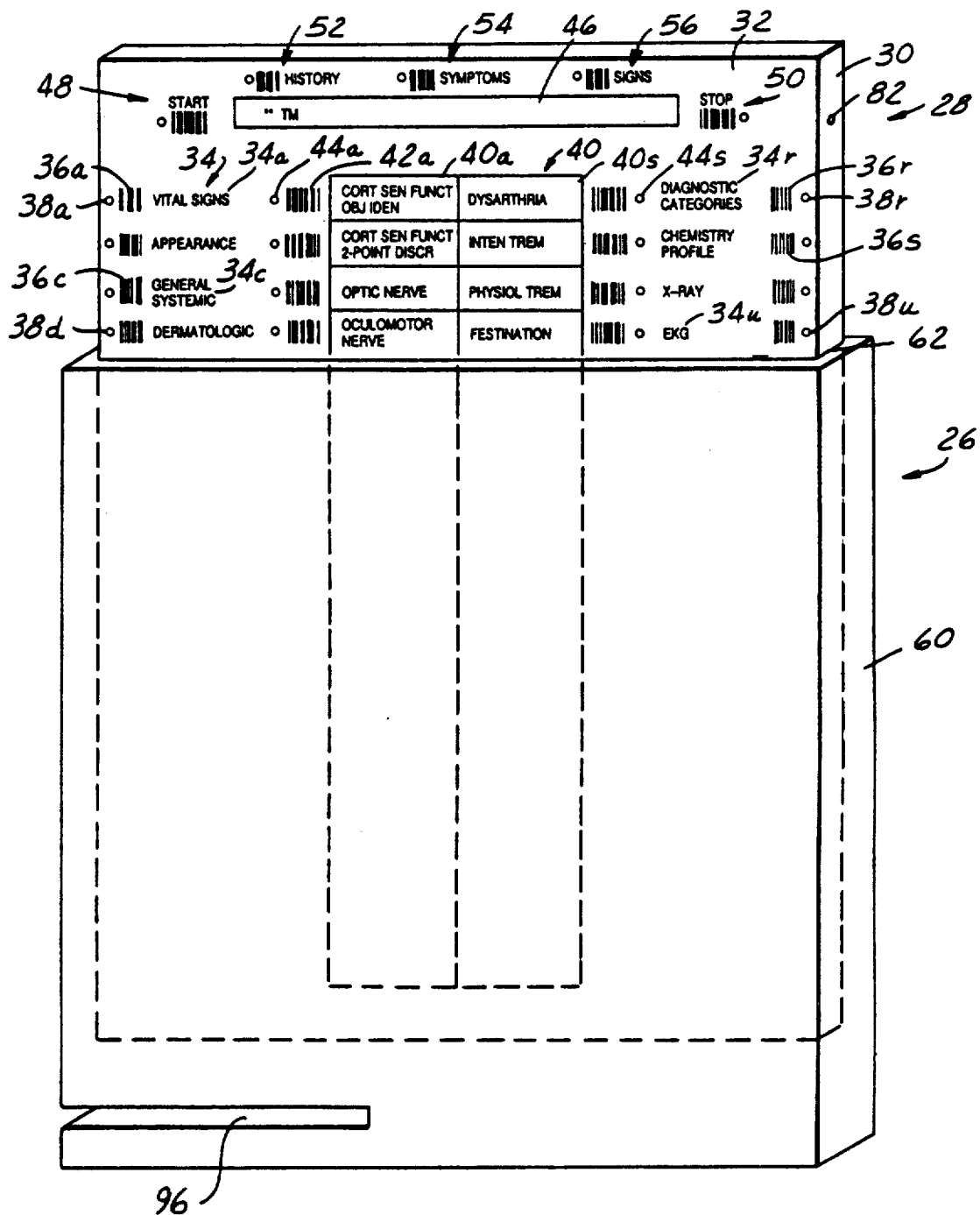
FIG. 2 is a perspective view of apparatus in accordance with a presently preferred embodiment of the invention.

As shown in FIG. 2, penboard 28 comprises a flat rectangular enclosure 30 having a front panel 32 for displaying examination information and prompting data input by the physician. Referring to both FIGS. 2 and 4, panel 32 includes a first display 34 listing general examination categories 34a–34ff along opposed side edges of panel 32. Preferably, category display 34 comprises general information diagnosis categories identified by suitable indicia permanently and legibly printed along the left-hand panel side edge—e.g., "vital signs" 34a, "appearance" 34b, "cardiovascular" 34e and "neurologic-1" 34 m. Likewise, general examination and treatment categories 34r–34ff are permanently and legibly printed in suitable indicia along the right-hand edge of panel 32—e.g., "chemistry profile" 34s, "medications" 34z and "follow-up" 34ee. Immediately adjacent to each examination indicia 34a–34ff, there appears a bar code 36a–36ff for uniquely optically identifying the corresponding adjacent category. Likewise, an LED 38a–38ff appears immediately adjacent to each category indicia 34a–34ff for indicating the general examination category selected by a physician.

Centrally of panel 32, there is positioned a liquid crystal display (LCD) 40 consisting of a multiplicity of individually-controlled display segments 40a–40jj configured in two adjacent rows. As will be described in detail hereinafter, the several segments of LCD 40 display specific examination indicia coordinated with the individual general examination (diagnosis or treatment) category 34 selected by the physician. Immediately outwardly adjacent to each display segment 40a–40jj, there is positioned a corresponding bar code segment 42a–42jj for uniquely identifying the corresponding display segment, and an LED 44a–44jj for indicating to the physician the display segments selected. Along the top edge of panel 32, there is provided a central elongated LCD 46 for indicating the patient's name; indicia, bar codes and LEDs 48a–c and 50a–c for indicating "start" and "stop" of data entry respectively; and indicia, bar codes and LEDs 52a–c, 54a–c and 56a–c for indicating entry of diagnostic "history", "symptoms" and "signs" respectively. Dataport 26 (FIG. 2) comprises a generally rectangular housing 60 having an open upper edge 62 for removably receiving penboard 32, and suitable means (not shown) on the rear face for mounting housing 60 on a wall or the like.

Figure 3:
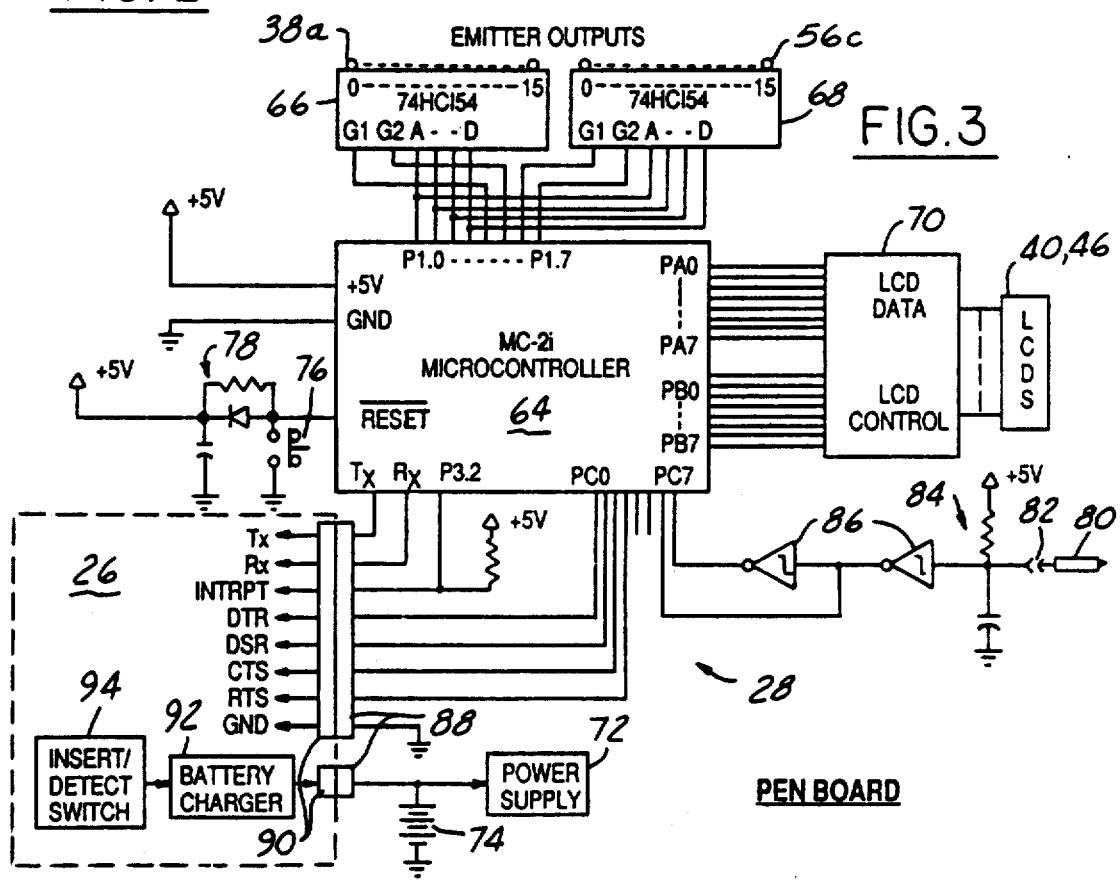
FIG. 3 is a functional block diagram of apparatus electronics in accordance with the presently preferred embodiment of the invention.

Referring to FIG. 3, penboard 28 internally includes a microprocessor-based controller 64 with internal memory having prestored therein sets of specific examination indicia for display at segments 40a–40jj of LCD 40 and associated with each general examination category 34a–34ff. Controller 64 also includes suitable memory space for storing patient examination information as will be described, and control programming for operating panel 32, receiving and storing patient examination data, and subsequently transmitting or downloading such data through dataport 26 to central computer 14 (FIG. 1). Microcontroller 64 has output ports P1.0–P1.7 connected through LED drivers 66, 68 to drive LEDs 38a–38ff and 48c–56c on panel 32. Likewise, microcontroller 64 has output ports PA0–PB7 connected through an LCD data and control driver 70 for driving LCD 46 and the several segments 40a–4jj of LCD 40. Microcontroller 64 and the remainder of the penboard circuitry receive power from a power supply 72 coupled to a battery 74 contained within penboard enclosure 30 (FIG. 2). A reset input to microcontroller 64 is coupled to an operator pushbutton 76, and to a delay circuit 78 for resetting the microcontroller on the initial power-up.

A further input to microcontroller 64 is received from a light pen 80 that is manipulated by the physician for scanning one or more bar codes on panel 32. Light pen 80 is connected through a socket 82 (FIGS. 2 and 3) on a sidewall of enclosure 30, through filtering circuitry 84 (FIG. 3) and through Schmitt triggers 86 to ports PC6 and 7 of microcontroller 64. The input/output ports PC0 and PC3 of microcontroller 64 are coupled to a connector 88 positioned at the lower edge of penboard 28, as are the transmit/receive and interrupt ports of the microcontroller. A mating connector 90 is internally positioned at the lower portion of dataport housing 60 for mating engagement with connector 88 when penboard 28 is fully inserted into dataport 26, as shown in FIG. 2. The input/output data and control ports of microcontroller 64 are thus connected through dataport 26 to central computer 14 (FIG. 1) for downloading patient examination information and/or uploading modified control programming to the penboard. A battery-charger 92 within dataport 26 is responsive to a switch 94 for detecting insertion of penboard 28 to recharge penboard battery 74 through connectors 90, 88. As shown in FIG. 2, dataport housing 60 also includes a slot 96 at the lower edge thereof for selectively receiving penboard 28 so as to mate connectors 88, 90 for downloading patient data without inserting penboard 28 into dataport 26.

Figure 4:
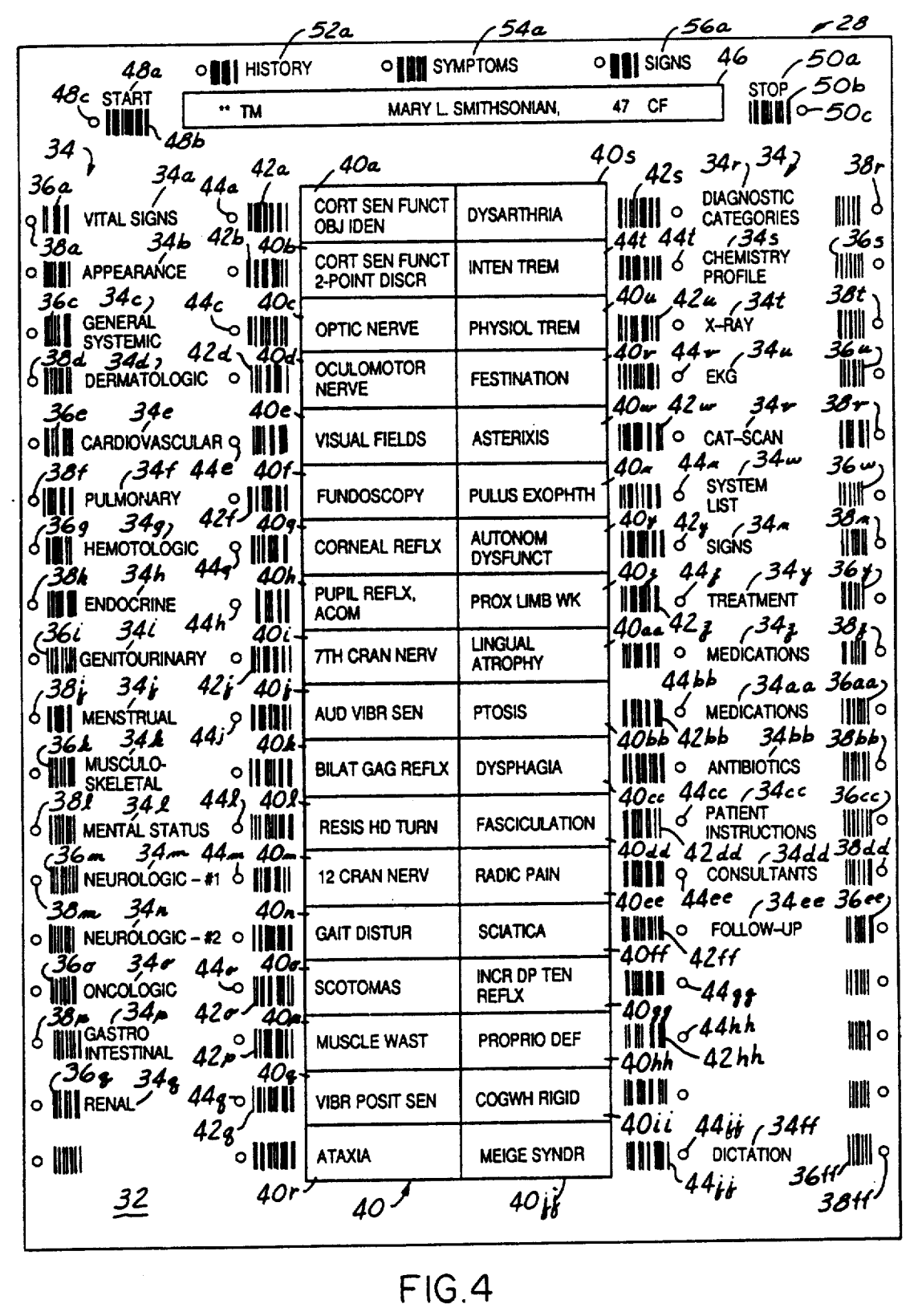

As previously noted, penboard 28 in the preferred embodiment of the invention has general examination category indicia 34a14 34ff permanently preprinted along with the side edges of panel 32. The general category indicia illustrated in FIGS. 2 and 4 represent suitable examination categories for a general practice physician. It will be noted that a number of blank spaces are provided in general information category display 34 for entry of suitable general examination or treatment categories as desired by the individual practitioner. Penboard 28 also has specific examination indicia prestored in microcontroller 64 coordinated with each general examination category. In addition, through central computer 14, the physician may add or modify specific examination indicia to be displayed at LCD 40. The specific indicia at display 40 illustrated in FIGS. 2 and 4 correspond to "neurologic" general examination category 34 m. The following Table 1 lists penboard display abbreviations 40a–40jj and the corresponding text which would be printed on chart note 16 (FIG. 1) for the patient file copy:

TABLE 1

| PENBOARD SCREEN ABBREVIATION | CHART-NOTE PRINTOUTS GENERATED BY SCREEN ABBREVIATION SELECTION |
|---|---|
| CORT SEN FUNCT | CORTICAL SENSORY FUNCTION |
| OBJ IDEN | OBJECT IDENTIFICATION INTACT |
| CORT SEN FUNCT 2-POINT DISCR | CORTICAL SENSORY FUNCTION |
| OPTIC NERV | OPTIC NERVE FUNCTION INTACT |
| OCULOMOTOR NERV | OCULOMOTOR NERVE WITHOUT IMPAIRMENT |
| VISUAL FIELDS INTACT | VISUAL FIELDS BILATERALLY |
| FUNDOSCOPY | FUNDOSCOPIC EXAM SHOWS NORMAL RETINAL PATTERN |
| CORNEAL REFLX | CORNEAL REFLEX BILATERALLY INTACT |
| PUPIL RELFX, ACOM | PUPILS ACCOMMODATE WITH INTACT REACTIVITY TO LIGHT |
| 7TH CRAN NERV | NO FACIAL ASYMMETRY OR WEAKNESS DURING CONVERSATION |
| AUD VIBR SEN | AUDITORY AND VIBRATORY SENSATION |
| BILAT GAG REFLX | BILATERAL GAG REFLEX NORMAL |
| RESIS HD TURN | RESISTANCE TO HEAD TURNING DEMONSTRATES INTACT IITH CRANIAL NERVE |
| 12TH CRAN NERV | NO ATROPHY, FASCICULATIONS, DEVIATION OF TONGUE |
| GAIT DISTUR | UNSTEADY WEAVING GAIT |
| SCOTOMAS | NEGATIVE SCOTOMA WITH CENTRAL FIELD INVOLVEMENT INTERFERRING WITH VISUAL ACUITY |
| MUSCLE WAST | DECREASED MUSCLE BULK OUT OF PROPORTION TO WEAKNESS |
| VIBR POSIT SEN | VIBRATORY POSITION SEND INTACT |
| ATAXIA | REELING WIDE-BASED GAIT |
| DYSARTHRIA | DIMINISHED ABILITY TO PRONOUNCE WORDS WITH NO EVIDENCE OF APHASIA |
| INTEN TREM | INTENTIONAL TREMOR |
| PHYSIOL TREM | NORMAL FINE, RAPID TREMOR |
| FESTINATION | FESTINATING GAIT |
| ASTERIXIS | COARSE, SLOW, NON-RHYTHMIC TREMOR - LIVER FLAP |
| PULS EXOPHTH | PULSATING EXOPHTHALMOS |
| AUTONOM DYSFUNCT | BLOOD PRESSURE FLUCTUATIONS, CARDIAC ARRHYTHMIAS, PUPILLARY CHANGES |

TABLE 1-continued

| PENBOARD SCREEN ABBREVIATION | CHART-NOTE PRINTOUTS GENERATED BY SCREEN ABBREVIATION SELECTION |
|---|---|
| PROX LIMB WK | PROXIMAL LIMB WEAKNESS |
| LINGUAL ATROPHY | LINGUAL ATROPHY |
| PTOSIS | PTOSIS RT/LT EYELID |
| DYSPHAGIA | DYSPHAGIA |
| FASCICULATION | FASCICULATION R/O LOWER MOTOR NEURON DISEASE |
| RADIC PAIN | RADICULAR PAIN |
| SCIATICA | RADIATING RT/LEFT SCIATIC PAIN |
| INCR DP TEN REFLX | HYPERACTIVE DEEP TENDON REFLEXES |
| PROPRIO DEF | PROPRIOCEPTIVE DEFICIT |
| COGWH RIGID | COGWHEEL RIDGIDTIY SUGGESTIVE OF PARKINSON'S DISEASE |
| MEIGE SYNDR | INVOLUNTARY BLINKING OF EYES AND JAW-GRINDING MOVEMENTS |

Likewise, the following Table 2 lists penboard display abbreviations appearing at LCD 40, and corresponding chartnote text, for "cardiovascular" general examination through category 34e:

TABLE 2

| PENBOARD SCREEN ABBREVIATION | CHART-NOTE PRINTOUTS GENERATED BY SCREEN ABBREVIATION SELECTION |
|---|---|
| ATRIAL PREM BEAT | ATRIAL PREMATURE BEATS |
| VENTR PREM CONTR | VENTRICULAR PREMATURE CONTRACTION |
| ATHER COR VESSEL | ATHEROSCLEROTIC CORONARY VESSEL DISEASE |
| CONGEST FAILURE | CONGESTIVE HEART FAILURE |
| LT BUN BR BLOCK | LEFT BUNDLE BRANCH BLOCK |
| MITRAL REGUR | MITRAL VALVE REGURGITATION |
| MITRAL STENOSIS | MITRAL VALVE STENOSIS |
| APEX BEAT | APEX BEAT ENLARGE & PROLONGED IN SITTING POSITION |
| INTERMITT CLAUD | INTERMITTENT CLAUDICATION |
| PAROXY NOC DYS | PAROXYSMAL NOCTURNAL DYSPNEA |
| PUL HYPERTEN | PULMONARY HYPERTENSION |
| SICK SINUS SYNDER | SICK SINUS SYNDROME (SSS) TACHYCARDIA-BRADYCARDIA |
| SUBAORT STENOSIS | SUBAORTIC STENOSIS |
| AORTIC EJECT SD | AORTIC EJECTION SOUND |
| SYSTOL CLICK | SYSTOLIC CLICK SUGGESTING |
| M V PROLAP | MITRAL VALVE PROLAPSE |
| SINGLE S2 NOR VAR | SINGLE S2 - NORMAL VARIATION |
| EPIGAST PULSAT | EPIGASTRIC PULSATION |
| ORTHO DECR BP | ORTHOSTATIC DECREASED BLOOD PRESSURE |
| CAROTID PULSE | CAROTID PULSE WITHIN NORMAL LIMITS |
| PANSYST REG MUR | PANSYSTOLIC REGURGITANT MURMUR |
| EARLY DIASTOL MUR | EARLY DIASTOLIC MURMUR AT BASE AND STERNAL BORDER |
| MID DIASTOL MUR | MID DIASTOLIC MURMUR AT APEX |
| COSTOCH TEND | TENDERNESS TO PALPATION OVER COSTOCHRONDRAL ARTICULATIONS (TIETZE'S SYNDROME) |
| LANCIN CHT PAIN | FLEETING, LANCINATING CHEST PAIN UNRELATED TO EFFORT OR EMOTIONAL EXCITEMENT, NOT INDICATING ANGINA |
| PARADOX SPLIT S2 | PARADOXICAL SPLITTING OF S2 |
| PAROXY TACH RECUR | PAROXYSMAL TACHYCARDIAS, RECURRENT R/O DIGITALIS INDUCED |
| PERICARD FRIC RUB | PERICARDIAL FRICTION RUB - AUDIBLE OVER THE PRECORDIUM, INCR. ON INSPIRATION |
| NORM 3RD SOUND | VENTRICULAR GALLOP, S3, NORMAL FOR PATIENT UNDER 30 YRS |
| CANNON SOUNDS | CANNON SOUNDS SUGGESTIVE OF AV |
| AV DISSOC/BLK | DISSOCIATION OR COMPLETE AV BLOCK |
| JUG VEN PUL | NORMAL RANGE 7-9 CM WITH A WAVE |

TABLE 2-continued

| PENBOARD SCREEN ABBREVIATION | CHART-NOTE PRINTOUTS GENERATED BY SCREEN ABBREVIATION SELECTION |
| --- | --- |
| WAVE | SYNCHRONOUS WITH S1 AND A SYNCHRONOUS WITH S2 |
| S1 & S2 WNL | FIRST AND SECOND HEART SOUNDS NORMAL SPLITTING |
| FIXED SPLIT S2 | FIXED SPLITTING OF S2 |
| S4 PRECD S1 LVH | S4 PRECEEDING S1, LIKELY INDICATING LEFT VENTRICULAR HYPERTROPHY |
| S3 IN DIASTROL | S3 IN DIASTOLE |
| ORTHOPNEA | ORTHOPNEA, MODERATELY SEVERE |
| INC CARD DULL | INCREASED CARDIAC DULLNESS |
| SINUS TACHY 100-150 | SINUS TACHYCARDIA 100-150 BEATS/MIN |
| ATRIAL FLUTTER 220-350 | ATRIAL FLUTTER 220-350 BEATS/MIN |

Indicia and text for the other general examination (diagnosis and treatment) categories may be selected and/or modified as desired.

With all such information prestored in penboard 28 and penboard battery 74 (FIG. 3) fully charged, the penboard is now ready for use by the physician in examining a patient. The examining physician first employs light pen 80 to scan a bar code or other suitable indicia on the patient file, resulting in storage of patient identification data in penboard microcontroller 64 and display of the patients' name at LCD 46 (FIGS. 2 and 4). The physician then scans bar code 48b with the light pen to indicate commencement of a data-entry process, and LED 48c is correspondingly illuminated. Assuming that the physician is examining the patient for a neurological disorder, the physician first scans bar code 36 m (FIG. 4) to indicate examination in general category 34 m. Specific examination indicia as shown in FIG. is then displayed at LCD segments 40a-40jj, and LED 38 m is illuminated to remind the physician that general examination category 34 m is under study. The physician then scans one or more bar codes 42a-42jj reflecting examination L of the patient, with LEDs 44a-44jj being illuminated as appropriate. In the event that one of the specific examination indicia 40a-40jj is incorrectly selected, the physician may rescan the corresponding bar code, whereupon selection is cancelled and the LED is extinguished. The physician may then select another (diagnosis or treatment) category and repeat the specific display selection process. If the physician wishes to dictate information for the patients' file not reflected in the prestored indicia, bar code 36ff is scanned during the examination process. When data-entry is complete, the physician scans bar code 50b and LED 50c is illuminated.

When examination is complete, penboard 28 is returned to dataport 26 so that connectors 88, 90 (FIG. 3) are brought into mating engagement. The patient information stored in microcontroller 64 is then downloaded to central computer 14 (FIG. 1) for preparation of file charts, prescription forms, etc. The penboard may alternatively be inserted into dataport slot 96 (FIG. 2) for transmission of patient data and reset pushbutton 76 (FIG. 3) may be depressed to reset the microcontroller, whereupon penboard 28 is ready for examination of a new patient. Suitable software for operating central computer 14 and microcontroller 64 in the manner described will be self-evident to the artisan.

Although the self-contained examination guide and information storage apparatus has been described in conjunction with a presently preferred embodiment thereof, it will be readily appreciated that modifications may be implemented without departing from the general principles of the invention. For example, although the invention has been described in connection with the presently preferred implementation for assisting patient examination by a physician, the invention in its broadest aspects may be readily applied to other types of examination or inspection processes. For example, penboard 28 may be configured for inspection of automobile engines, with general inspection categories such as "carburetor", "valve timing", etc. being listed along with outside edges of the penboard panel, and specific examination indicia such as "idle screw adjust" displayed at LCD 40 as a function of selected general examination category. While use of a light pen 80 and of bar codes on the penboard is presently preferred both for reasons of reliability and because the light pen may also be employed to scan patient identification data on the patient file, other means for entering general and specific examination information may be employed, such as membrane switches or the like positioned in place of the various bar codes adjacent to the indicia as shown in FIGS. 2 and 4. Communication at connectors 88, 90 (FIG. 3), with penboard 28 inserted in either dataport top 62 or slot 96 (FIG. 2), may be by direct mechanical connection and electrical transmission, or by alignment of optical couplers for fiberoptic transmission.

The invention claimed is:

1. Self-contained examination guide and information storage apparatus comprising:

a flat rectangular enclosure having a flat front panel with parallel side edges, first display means on said front panel disposed along at least one side edge of said panel bearing fixed indicia associated with a plurality of general examination categories, a plurality of means individually disposed on said panel adjacent to associated ones of said first display means and individually permanently associated with said general examination categories for selecting among said general examination categories, second display means position on said front panel between said side edges, said second display means being distinct from said first display means and including a plurality of individually alterable display segments, means within said enclosure responsive to said category-selecting means for displaying a plurality of specific examination indicia at said display segments, said plurality of specific examination indicia being coordinated with each said general examination category, a plurality of means individually disposed on asid panel adjacent to an associated display segment for selectively identifying specific examination indicia of interest, and means within said enclosure responsive to said selectively-identifying means for storing specific examination indicia associated with each said general examination category.

2. The apparatus set forth in claim 1 wherein said means responsive to said category selecting means comprises microprocessor-based control means including memory having prestored therein sets of said specific examination indicia, and means responsive to said category-selecting means for retrieving from said memory a specific set of examination indicia associated with a selected general examination category and displaying said set at said second display means.

3. The apparatus set forth in claim 2 wherein said microprocessor-based control means further includes means for selectively altering said specific examination indicia associated with each said set.

4. The apparatus set forth in claim 1 further comprising means for selectively retrieving information stored in said indicia-storing means.

5. The apparatus set forth in claim 4 wherein said selectively-retrieving means comprises central information storage and processing means separate from said indicia-storing means, and a dataport coupled to said central means and including means for selective connection to said indicia-storing means.

6. The apparatus set forth in claim 1 wherein said means responsive to said category-selecting means and said indicia-storing means comprise microprocessor-based control means.

7. The apparatus set forth in claim 6 wherein said microprocessor-based control means includes means for selectively retrieving information stored in said indicia-storing means.

8. The apparatus set forth in claim 7 wherein said selectively-retrieving means comprises central information storage and processing means, and a dataport coupled to said central means and including means for selective connection to said indicia-storing means.

9. The apparatus set forth in claim 8 wherein said selectively-retrieving means comprises connectors on said dataport and said enclosure adapted for mating engagement for selectively directly connecting said microprocessor-based control means to said central means.

10. The apparatus set forth in claim 9 further comprising battery means contained within said enclosure for supplying electrical power to said apparatus, and a battery charger contained within said dataport and adapted for connection to said battery means through said connectors.

11. The apparatus set forth in claim 1 wherein said second display means comprises a multiple-segment LCD.

12. The apparatus set forth in claim 1 further comprising means associated with and adjacent to each said display segment, and responsive to said selectively-identifying means, for indicating selection of examination indicia in that segment by said selectively-identifying means.

13. The apparatus set forth in claim 1 wherein said category-selecting means and said selectively-identifying means comprise a light pen and a multiplicity of bar code indicia associated with individual said general and specific examination indicia.

14. The apparatus set forth in claim 1 wherein said general examination indicia includes indicia associated with a plurality of medical examination categories, and wherein said specific examination indicia comprises signs associated with each said medical examination category.

15. Self-contained examination guide and information storage apparatus comprising:

a flat rectangular enclosure having a front panel, first display means on said panel bearing fixed indicia associated with a plurality of general examination categories, second display means on said front panel and including a plurality of individually alterable display segments, and microprocessor-based control means including means on said panel in fixed position adjacent to said first display means for selecting among said general examination categories, memory means having prestored therein sets of specific examination indicia associated with each said general examination category, means responsive to said category-selecting means for retrieving from said memory means a set of said specific examination indicia associated with the selected general examination category, means for displaying said set at associated predetermined individual segments of said second display means, means on said panel in fixed position adjacent to individual segments of said second display means for selectively identifying specific examination indicia of interest at said second display means, and means responsive to said selectively-identifying means for storing information associated with selectively-identified specific examination indicia.

16. The apparatus set forth in claim 15 wherein said first display means comprises a plurality of indicia permanently affixed along side edges of said panel and individually associated with said plurality of examination categories, said category-selecting means comprising a plurality of category-selecting means individually disposed adjacent to associated said category indicia, and wherein said second display means comprises a multiple-segment LCD positioned on said panel between said side edges.

17. The apparatus set forth in claim 16 wherein said category-selecting means and said selectively-identifying means comprise a light pen and a multiplicity of bar code indicia associated with individual said general and specific examination indicia.

18. The apparatus set forth in claim 15 further comprising means associated with and adjacent to each said display segment, and responsive to said selectively-identifying means, for indicating selection of examination indicia in that segment by said selectively-identifying means.

19. The apparatus set forth in claim 18 wherein said indicia-indicating means comprises a plurality of LEDs, one associated with each said general and specific examination indicia.

20. The apparatus set forth in claim 15 further comprising central information storage and processing means, a dataport coupled to said central means and adapted for selective connection to said microprocessor-based control means, and means for selectively transmitting information stored in said storing means to said control means.

21. The apparatus set forth in claim 20 wherein said dataport comprises a generally rectangular housing having an open end adapted to receive said enclosure, and connectors positioned on said enclosure and said housing for mating engagement when said enclosure is inserted into said housing.

22. Self-contained examination guide and information storage apparatus comprising:
   a generally rectangular enclosure having a flat front panel,
   first display means on said front panel bearing indicia associated with a plurality of general examination categories,
   means on said front panel for selecting among said general examination categories,
   second display means on said front panel including a plurality of display segments,
   means on said front panel associated with each said display segment for selectively identifying specific examination indicia of interest,
   microprocessor-based control means housed within said enclosure and including means responsive to said category-selecting means for displaying a plurality of specific examination indicia at said display segments, said plurality of specific examination indicia being coordinated with each said general examination category, and means responsive to said selectively-identifying means for storing specific examination indicia associated with each said general examination category,
   means for selectively retrieving information stored in said indicia-storing means including central information storage and processing means, a dataport coupled to said central means, connectors on said dataport and said enclosure adapted for mating engagement for selectively directly connecting said indicia-storing means in said microprocessor-based control means to said central means,
   battery means within said enclosure for supplying electrical power to said apparatus, and
   a battery charger contained within said dataport and adapted for connection to said battery means through said connectors.

23. The apparatus set forth in claim 22 wherein said dataport comprises a generally rectangular housing having an open end adapted to receive said enclosure, said connectors being positioned on said enclosure and said housing for mating engagement when said enclosure is inserted into said housing.

24. The apparatus set forth in claim 23 further comprising a slot in a sidewall of said housing and a connector positioned in said housing adjacent to said slot for connecting said microprocessor-based control means to said central means without inserting said enclosure into said housing.

25. Self-contained examination guide and information storage apparatus comprising:
   a flat rectangular enclosure having a front panel,
   first display means permanently affixed along side edges of said panel bearing indicia associated with a plurality of general examination categories,
   second display means including a multiple-segment LCD positioned on said panel between said side edges,
   microprocessor-based control means including means on said panel for selecting among said general examination categories, memory means having pre-stored therein sets of specific examination indicia associated with each said general examination category, means responsive to said category-selecting means for retrieving from said memory means a set of said specific examination indicia associated with the selected general examination category, means for displaying said set at said second display means, means on said panel for selectively identifying specific examination indicia of interest, and means responsive to said selectively-identifying means for storing information associated with selectively-identified specific examination indicia,
   central information storage and processing means,
   a dataport coupled to said central means and adapted for selective connection to said microprocessor-based control means, said dataport comprising a generally rectangular housing having an open end adapted to receive said enclosure, and connectors positioned on said enclosure and said housing for mating engagement when said enclosure is inserted into said housing, and
   means for selectively transmitting information stored in said storing means to said control means.

26. The apparatus set forth in claim 25 further comprising battery means contained within said enclosure for supplying electrical power to said apparatus, and a battery charger contained within said dataport and adapted for connection to said battery means through said connectors.

27. The apparatus set forth in claim 26 wherein said general examination indicia includes indicia associated with a plurality of medical examination categories, and wherein said specific examination indicia comprises signs associated with each said medical examination category.

28. The apparatus set forth in claim 27 wherein said central means including means for preparing hard copies of information transmitted from said microprocessor-based control means for inclusion in patient files.

29. A method of collecting examination data and entering said data in a computer including a central computer, at least one dataport coupled with said central computer, the central computer including a memory, the dataport being separate from the central computer but coupled with the memory of the central computer, and at least one portable data entry means including a memory having stored therein a plurality of examination categories and for each category a set of examination indicia, a panel having display means thereon identifying code means adjacent said categories and said indicia, and input means connected to said memory of said data entry means, said method comprising the steps of:
   (a) entering in said memory of said portable data entry means an identification of a subject of examination;
   (b) selecting an examination category from said plurality and entering said selected category in said memory of said data entry means;
   (c) entering examination indicia of said set for said selected category in said memory of said data entry means;
   (d) displaying said examination categories and said examination indicia in asid display means, (e) entering said selected category and said examination indicia by moving said input means adjacent said code means, and (f) coupling said data entry means with said dataport and downloading stored data from said memory of said data entry means to said memory of said central computer.

30. The method set forth in claim 29 further including the step of adding or modifying examination indicia in said memory of said data entry means by entering additions or modifications in said central computer while said data entry means is coupled with said dataport.

31. The method set forth in claim 30, further including the step of operating said central computer to print said examination data.

32. A method of conducting an examination of a subject with the aid of a portable data entry means having a memory therein, a panel having display means and, identifying code means thereon, and input means connected to said memory of said data entry means, comprising:

(a) providing said memory with a database including a plurality of examination categories and for each category a set of examination indicia said identifying code means on said panel being adjacent to said categories and said indicia;

(b) reviewing a subject of examination, selecting an examination category, entering said selection in said memory, retrieving from said memory the set of examination indicia associated with said selected category and displaying on said portable data entry means the set of examination indicia;

(c) reviewing the subject of examination, selecting indicia from said set, and entering said selected indicia in said;

(d) displaying said examination categories and said examination indicia in said display means, (e) entering said selected category and said examination indicia by moving said input means adjacent said code means, (f) downloading data from said memory into a central computer.

33. The method set forth in claim 32, and further including the step of operating said central computer to print said examination data.

34. A computerized examination system comprising:

(a) a central computer including a memory and printer means;

(b) at least one dataport separate from said central computer, said dataport including first connector means coupled to said central computer; and (c) a portable data entry means separate from said central computer and said dataport and comprising:

(1) a portable enclosure;

(2) a memory in said enclosure having stored therein a plurality of examination categories and for each category a set of examination indicia;

(3) second connector means on said enclosure and connectable with said first connector means for transferring data between said memories of said central computer and said data entry means; and (4) display and input means on said enclosure for displaying said categories and said indicia and for selectively entering said categories and said indicia in said memory in said portable enclosure, (5) said display and input means comprising a printed display of said categories and a changeable display of said indicia, identifying code means adjacent said printed and changeable displays, and input means connected to said memory in said portable enclosure and responsive to said code means.

35. Apparatus for use in a computerized examination system having a central computer including a memory and printer means, at least one dataport separate from said central computer, said dataport including first connector means coupled to said central computer, said apparatus being separate from said central computer and said dataport and comprising:

(1) a portable enclosure;

(2) a memory in said enclosure having stored therein a plurality of examination categories and for each category a set of examination indicia;

(3) second connector means on said enclosure and connectable with said first connector means for transferring data between said memories of said central computer and said apparatus; and (4) display and input means on said enclosure for displaying said categories and said indicia and for selectively entering said categories and said indicia in said memory in said portable enclosure, (5) said display and input means comprising a printed display of said categories and changeable display of said indicia, identifying code means adjacent said printed and changeable displays, and input means connected to said memory in said portable enclosure and responsive to said code means.

36. Apparatus for use in a computerized examination system, comprising:

(a) a portable enclosure:

(b) a memory mounted on said enclosure;

(c) a list of examination categories on said enclosure;

(d) first input means connected to said memory for entering therein a selection of one of said categories;

(e) display panel means on said enclosure and connected to said memory;

(f) said memory having stored therein a set of examination indicia associated with each of said categories, and selection of said one of said categories causing said set of indicia associated therewith to be shown in said display panel means;

(g) second input means connected to said memory for entering therein data relating to said indicia; and (h) port means on said enclosure and connected to said memory for transferring data between said memory and said central computer;

(i) said first input means comprising first code means on said enclosure and pen means responsive to said first code means, and said second input means comprising second code means on said enclosure and said pen means.

37. Apparatus as set forth in claim 36 further including a dataport adapted to be electronically connected to the central computer, said port means being engagable with said dataport for said transfer of said data.

* * * * *